US011186782B2

(12) United States Patent
Peitz et al.

(10) Patent No.: US 11,186,782 B2
(45) Date of Patent: Nov. 30, 2021

(54) CATALYST AND PROCESS FOR REMOVING MERCAPTANS FROM HYDROCARBON STREAMS

(71) Applicant: Evonik Operations GmbH, Essen (DE)

(72) Inventors: Stephan Peitz, Oer-Erkenschwick (DE); Helene Reeker, Dortmund (DE); Reiner Bukohl, Marl (DE); Thomas Quandt, Marl (DE); Stefan Röder, Sinntal (DE); Armin Matthias Rix, Marl (DE); Andreas Wolff, Recklinghausen (DE); Guido Stochniol, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 68 days.

(21) Appl. No.: 16/722,127

(22) Filed: Dec. 20, 2019

(65) Prior Publication Data
US 2020/0216763 A1   Jul. 9, 2020

(30) Foreign Application Priority Data
Jan. 8, 2019 (EP) .................................... 19150660

(51) Int. Cl.
| | | |
|---|---|---|
| *C10G 29/04* | (2006.01) |
| *B01J 23/44* | (2006.01) |
| *B01J 35/10* | (2006.01) |
| *C07C 319/18* | (2006.01) |
| *C10G 55/06* | (2006.01) |
| *B01J 21/04* | (2006.01) |
| *B01J 21/08* | (2006.01) |
| *B01J 21/18* | (2006.01) |

(52) U.S. Cl.
CPC .............. *C10G 29/04* (2013.01); *B01J 23/44* (2013.01); *B01J 35/1009* (2013.01); *C07C 319/18* (2013.01); *C10G 55/06* (2013.01); *B01J 21/04* (2013.01); *B01J 21/08* (2013.01); *B01J 21/18* (2013.01); *C07C 2521/04* (2013.01); *C07C 2521/08* (2013.01); *C07C 2521/18* (2013.01); *C07C 2523/44* (2013.01); *C10G 2300/1092* (2013.01); *C10G 2300/202* (2013.01)

(58) Field of Classification Search
None
See application file for complete search history.

(56) References Cited

U.S. PATENT DOCUMENTS

| | | |
|---|---|---|
| 5,851,383 A | 12/1998 | Frey |
| 7,939,597 B2 | 5/2011 | Bub et al. |
| 8,198,481 B2 | 6/2012 | Kuppinger et al. |
| 8,258,249 B2 | 9/2012 | Bub et al. |
| 8,293,941 B2 | 10/2012 | Kuppinger et al. |
| 8,481,784 B2 | 7/2013 | Kuppinger et al. |
| 8,524,945 B2 | 9/2013 | Stochniol et al. |
| 8,859,834 B2 | 10/2014 | Boeing et al. |
| 8,895,683 B2 | 11/2014 | Kuppinger et al. |
| 9,260,386 B2 | 2/2016 | Peitz et al. |
| 9,856,184 B2 | 1/2018 | Stochniol et al. |
| 10,125,089 B2 | 11/2018 | Kohlstruk et al. |
| 10,189,755 B2 | 1/2019 | Reeker et al. |
| 10,196,327 B2 | 2/2019 | Stochniol et al. |
| 10,227,279 B2 | 3/2019 | Stochniol et al. |
| 10,245,578 B2 | 4/2019 | Klasovsky et al. |
| 2006/0276334 A1 | 12/2006 | Balduf et al. |
| 2009/0068440 A1 | 3/2009 | Bub et al. |
| 2010/0190638 A1 | 7/2010 | Hagemeyer et al. |
| 2018/0230081 A1 | 8/2018 | Rüfer et al. |
| 2018/0339959 A1 | 11/2018 | Rittsteiger et al. |
| 2019/0283003 A1 | 9/2019 | Nadolny et al. |
| 2019/0283004 A1 | 9/2019 | Nadolny et al. |
| 2019/0283005 A1 | 9/2019 | Nadolny et al. |
| 2019/0283006 A1 | 9/2019 | Nadolny et al. |

FOREIGN PATENT DOCUMENTS

| | | |
|---|---|---|
| CA | 3 016 807 A1 | 9/2017 |
| DE | 10 2007 025356 A1 | 1/2009 |
| DE | 10 2012 212 317 A1 | 1/2014 |
| WO | 2012/004081 A1 | 1/2012 |

OTHER PUBLICATIONS

Nadolny et al., U.S. Appl. No. 16/509,532, filed Jul. 12, 2019.
Peitz et al., U.S. Appl. No. 16/713,301, filed Dec. 13, 2019.
European Search Report dated Jul. 23, 2019 in EP 19150660.9 (9 pages).

*Primary Examiner* — Colin W. Slifka
(74) *Attorney, Agent, or Firm* — Taylor English Duma LLP; Philip P. McCann

(57) ABSTRACT

The invention relates to a catalyst for a process for removing mercaptans and optionally disulfides (if present) from hydrocarbon streams, in particular C4 streams, in the presence of higher dienes, in particular C5 dienes. At the same time, the invention also relates to a process for removing mercaptans and disulfides (if present) from hydrocarbon streams, in particular C4 streams, in one embodiment in the presence of 1-butene, by thioetherification of the mercaptans with polyunsaturated hydrocarbons, wherein the process is carried out in a reactor with addition of hydrogen in the presence of higher dienes, in particular $C_5$ dienes.

20 Claims, No Drawings

CATALYST AND PROCESS FOR REMOVING MERCAPTANS FROM HYDROCARBON STREAMS

CROSS REFERENCE TO RELATED APPLICATIONS

This application is a 35 U.S.C. § 119 patent application which claims the benefit of European Application No. 19150660.9 filed Jan. 8, 2019, which is incorporated herein by reference in its entirety.

FIELD

The invention relates to a catalyst for a process for removing mercaptans and optionally disulfides from hydrocarbon streams, in particular C4 streams, in the presence of higher dienes, in particular C5 dienes. At the same time, the invention also relates to a process for removing mercaptans from hydrocarbon streams, in particular C4 streams, in one embodiment in the presence of 1-butene, by thioetherification of the mercaptans with polyunsaturated hydrocarbons, wherein the process is carried out in a reactor with addition of hydrogen in the presence of higher dienes, in particular $C_5$ dienes.

BACKGROUND

Mixtures of C4 hydrocarbons are raw materials from downstream petrochemistry. They originate either from steam crackers (so-called "crack C4") or from fluid catalytic crackers (so-called "FCC C4"). Mixtures of C4 hydrocarbons of different origin are also traded, the so-called "C4 cut". For the purposes of utilizing the individual components, the C4 mixtures need to be split into their constituents with the highest possible purity.

Mercaptans are compounds of the class R—SH, where R is a hydrocarbon radical and S is sulfur and H is hydrogen. Mercaptans are also referred to as thiols. Important representatives of the mercaptans are methyl mercaptan and ethyl mercaptan, also respectively known as methanethiol and ethanethiol. In the context of the present invention, disulfides are organic compounds having an S—S bond. An important representative is dimethyl disulfide. Mercaptans occur as undesirable accompanying substances in C4 hydrocarbon mixtures at up to 200 ppm.

Industrial C4 hydrocarbon mixtures from catalytic crackers (FCC C4) or steam crackers (crack C4) typically contain not only saturated and monounsaturated compounds but also polyunsaturated compounds. Before individual compounds can be isolated from these mixtures, it is often necessary to remove other compounds as completely as possible. This can be done by physical methods, for example distillation, extractive distillation or extraction, but also by a selective chemical conversion of the components to be removed. Particular attention must be paid here to the fullest possible removal of the contaminants, such as oxygen-, nitrogen- and sulfur-containing components, present in the C4 hydrocarbon mixture, since these can have adverse effects on the individual process steps as catalyst poisons. Whereas these contaminants are typically present in crack C4 only in traces, in FCC C4 streams they may also be present in higher concentrations.

The composition of the raw materials can vary significantly according to the origin of the material. The listed C4 components are additionally accompanied by hydrocarbons having fewer or more carbon atoms and by small amounts of contaminants such as mercaptans, sulfides, disulfides and nitrogen- and oxygen-containing compounds.

FCC C4 may in one variant be worked up such that the concentration of isobutane is first lowered by means of a distillation step. At the same time, the low boilers present in the mixture (for example C3 hydrocarbons, light oxygen-, nitrogen- and sulfur-containing compounds) are removed or minimized. In the following step, which takes place in a column, all the high boilers (for example C5 hydrocarbons, heavy oxygen-, nitrogen- and sulfur-containing compounds) are removed via the bottom. In the next step, isobutene is removed, for example by reacting it with methanol to give methyl tert-butyl ether (MTBE), with the latter removed by distillation. If pure isobutene is to be obtained, the methyl tert-butyl ether can subsequently be cleaved to give isobutene and methanol.

For further workup of the C4 mixture, the polyunsaturated compounds still remaining must be converted into the corresponding monounsaturated compounds by means of a selective hydrogenation process. 1-Butene and remaining isobutane can then be removed by distillation in sufficient purity and the remaining 2-butenes and the n-butane subjected to further workup. Often, the 2-butenes are converted by dimerization into octenes, which are then converted into plasticizer alcohols through hydroformylation and hydrogenation. The saturated C4 hydrocarbons may be used for example as propellants for aerosols.

If the selective hydrogenation process before the removal of 1-butene does not reduce the concentration of polyunsaturated compounds to a value of less than 10 ppm, the purity requirements for 1-butene, which is used in polymerizations, are not met. Polyunsaturated compounds also suppress the catalytic activity of the catalysts for the dimerization of the 2-butenes.

The demands on the selectivities in the processes for the selective hydrogenation of polyunsaturated hydrocarbons are particularly high, because overhydrogenation, i.e. hydrogenation of monounsaturated compounds, or isomerization of terminal double bonds to internal double bonds results in the destruction of products of value. In the fine purification of streams that already have a low content of polyunsaturated compounds, the concentrations of polyunsaturated compounds must at the same time be further reduced to values below 10 ppm by weight.

In the case of catalytic C4 streams, what can now occur is that, in addition to the light sulfur-containing components, for example $H_2S$, COS or MeSH, already removed by distillation during removal of low boilers and the higher-boiling sulfur compounds such as dimethyl disulfide removed later in the C5 column, mercaptan-type intermediate boilers (for example ethanethiol) remain present. These cannot be readily removed from the $C_4$ stream by distillation. The presence of mercaptans during the workup of C4 streams is undesirable or interferes therewith.

If mercaptans (for example ethanethiol) and optionally disulfides are present in the feed for selective hydrogenation, they inhibit the catalytic conversion of 1,3-butadiene. This means that the branched polyunsaturated compounds may be present in the subsequent product (for example 1-butene) and jeopardize its purity. If the polyunsaturated compounds pass into the feed for the oligomerization of n-butenes as a consequence of the insufficient conversion in the selective hydrogenation caused by the mercaptan content, they deactivate the oligomerization catalyst.

It is known that feeding the selective hydrogenation catalyst with sulfur-containing components can result in the formation of hydroisomerization-active catalysts. The mercaptans present in the feed for the selective hydrogenation can result in the formation of such a hydroisomerization catalyst, leading to undesired isomerization of 1-butene to 2-butenes.

DE 10 2012 212 317 A1 accordingly proposes a process for the thioetherification of mercaptans with polyunsaturated hydrocarbons using a heterogeneous catalyst containing palladium as the catalytically active metal and with addition of hydrogen, which is used in a defined ratio to the polyunsaturated hydrocarbons. A detailed description of further prior art with regard to the removal of mercaptans from hydrocarbon streams is likewise given in DE 10 2012 212 317 A1.

However, the disadvantage of the catalyst used therein is that the thioetherification of the mercaptans is inhibited by the presence of higher dienes such as C5 dienes, in particular isoprene, and does not proceed to completion. This means that mercaptans such as ethanethiol and/or methanethiol remain in the hydrocarbon stream and can lead to the problems already described.

Moreover, disulfides such as dimethyl disulfide that are potentially present in the C4 stream are cleaved into two equivalents of methanethiol if isoprene and/or other long-chain polyunsaturated hydrocarbons are present at the same time. This results in the mercaptan content actually increasing rather than being reduced by thioetherification.

SUMMARY

The object of the present invention was therefore to provide a catalyst that, even in the presence of higher dienes, leads to (almost) complete conversion of the mercaptans and optionally disulfides (if present) present in the hydrocarbon stream, i.e. including mercaptans potentially additionally formed in situ by disulfide cleavage. A further object was to provide a process that is not subject to the abovementioned problems and that makes it possible for the thioetherification of the mercaptans in particular to proceed to completion.

The object is achieved by the inventive catalyst according to claim 1 and the process according to claim 6. Preferred embodiments are specified in the dependent claims.

DETAILED DESCRIPTION

The present invention provides a heterogeneous catalyst for removing mercaptans and optionally disulfides (if present) from hydrocarbon streams in the presence of higher dienes, wherein the catalyst is a shell catalyst, wherein the catalyst comprises alumina, silica gel or activated carbon as support material and palladium and platinum as catalytically active metals and wherein the catalyst has a palladium concentration of up to 2.0% by weight, preferably of up to 1.0% by weight, more preferably of up to 0.5% by weight, a platinum concentration of up to 1.0% by weight, preferably of up to 0.5% by weight, more preferably of up to 0.2% by weight and a total metal dispersion of at least 70%. The stated values for the palladium and platinum concentrations refer in each case to the total catalyst. The term shell catalyst refers to the form of the catalyst, in which the core consists of the support material on which a shell of Pd/PdO and Pt/PtO is applied by a spraying process and subsequent calcination, the layer thickness and depth of penetration into the support of said shell being only a few µm in each case.

The hydrocarbon stream preferably comprises C2 to C8 olefins, more preferably C3 to C6 olefins and most preferably C4 olefins. The hydrocarbon stream to be purified of mercaptans and disulfides (if present) is in particular a C4 hydrocarbon stream (C4 stream). Suitable olefins include α-olefins, n-olefins and cycloalkenes, preferably n-olefins. In a preferred embodiment, the olefin is n-butene. The olefins are usually not used in pure form, but as industrially available mixtures such as the mentioned crack C4 or FCC C4. The term hydrocarbon stream additionally used in this invention is therefore to be understood as meaning mixtures of any type that contain the relevant olefins in an amount that makes it possible to perform the possible process steps downstream of purification economically.

The term "higher diene" in the context of the present invention means at least C5 dienes or dienes having more than 5 carbon atoms. The higher diene is preferably a C5 diene, in particular isoprene. The dienes are typically present in low concentrations in the industrial hydrocarbon streams to be purified of mercaptans in accordance with the present invention. Higher dienes undergo reaction in the selective hydrogenation with greater difficulty than, for example, butadiene (see also WO 2012/004081 A1), which means that inhibition of the reaction by C5 dienes is plausible in the thioetherification too.

The catalyst used in the process of the present invention is a shell catalyst composed of a support material and palladium and platinum as the catalytically active metals, through which the mercaptans in the hydrocarbon stream can be converted completely into thioethers. The support material is, for example, alumina, silica gel or activated carbon. The support material used is preferably alumina.

The catalyst has a palladium concentration of up to 2.0% by weight, preferably of up to 1.0% by weight and more preferably of up to 0.5% by weight. The catalyst at the same time has a platinum concentration of up to 1.0% by weight, preferably of up to 0.5% by weight and more preferably of 0.2% by weight.

The inner surface area of the catalyst (determined by gas adsorption according to DIN ISO 9277) is preferably from 50 to 400 m$^2$/g, more preferably between 100 and 300 m$^2$/g and particularly preferably between 200 and 300 m$^2$/g.

In a preferred embodiment, the catalyst additionally has a total metal surface area (determined by CO pulse chemisorption according to AN-SOP 1954 version 1) of at least 0.5 m$^2$/g, preferably of at least 1.0 m$^2$/g and more preferably of at least 1.5 m$^2$/g. Total metal surface areas smaller than those indicated lead to a reduction in catalyst activity.

The catalyst according to the invention has a total metal dispersion of at least 70%, preferably of at least 80%. The total metal dispersion indicates how well the metals/metal oxides are dispersed on the surface. The dispersion on the surface can be controlled by the duration and the intensity of spraying of the support material with the Pd/Pt salt solution during the preparation of the catalyst. Dispersion here refers to a heterogeneous mixture of disperse phase (Pd/Pt) and dispersion medium (support). The higher the dispersion on the surface, the higher the activity of the catalyst. It was surprisingly found that complete conversion of the mercaptans cannot be achieved if the total metal dispersion is below 70%.

The present invention further provides a process for removing mercaptans and disulfides (if present) from hydrocarbon streams in the presence of at least one higher diene by thioetherification of the mercaptans with polyunsaturated hydrocarbons, wherein the process is carried out in a reactor with addition of hydrogen, wherein the molar ratio of hydrogen to polyunsaturated hydrocarbons is not more than one. The process uses the previously described heterogeneous catalyst comprising palladium and platinum as the catalytically active metals, wherein the catalyst has a palladium concentration of up to 2.0% by weight, preferably of up to 1.0% by weight, more preferably of up to 0.5% by weight, a platinum concentration of up to 1.0% by weight, preferably of up to 0.5% by weight, more preferably of up to 0.2% by weight and a total metal dispersion of at least 70%, preferably of at least 80%. The stated values for the palladium and platinum concentrations refer in each case to the total catalyst.

The hydrocarbon stream preferably comprises C2 to C8 olefins, more preferably C3 to C5 olefins and most preferably C4 olefins. The hydrocarbon stream to be purified of mercaptans is in particular a C4 hydrocarbon stream (C4 stream). Suitable olefins include α-olefins, n-olefins and cycloalkenes, preferably n-olefins. In a preferred embodiment, the olefin is n-butene. The olefins are usually not used in pure form, but as industrially available mixtures such as the mentioned crack C4 or FCC C4. The term hydrocarbon stream additionally used in this invention is therefore to be understood as meaning mixtures of any type that contain the relevant olefins in an amount that makes it possible to perform the possible process steps downstream of purification economically. The term "higher diene" in the context of the present invention means at least C5 dienes or dienes having more than 5 carbon atoms. The higher diene is preferably a C5 diene, in particular isoprene. The dienes are typically present in low concentrations in the industrial hydrocarbon streams to be purified of mercaptans in accordance with the present invention. Higher dienes undergo reaction in the selective hydrogenation with greater difficulty than butadiene (see also WO 2012/004081 A1), which means that inhibition of the reaction by C5 dienes is plausible in the thioetherification too.

Through the use of a heterogeneous catalyst comprising palladium and platinum as catalytically active metals, the process according to the invention is able to convert mercaptans into high-boiling thioethers with complete conversion while at the same time almost completely suppressing significant isomerization of 1-butene to internal butenes and completely preventing hydrogenation of the butenes. If 1-butene is present in the hydrocarbon stream in a concentration that is higher than the concentration at thermodynamic equilibrium for the double bond isomerization of 1-butene to 2-butene, the conversion of 1-butene into 2-butenes through isomerization and/or the hydrogenation to n-butane is preferably less than 5%, more preferably less than 3% and most preferably less than 2%.

It has been found that mercaptans in the presence of polyunsaturated hydrocarbons and hydrogen can be converted into higher-boiling thioethers to below the detection limit, while the isomerization of 1-butene is greatly suppressed and the hydrogenation of butenes is completely prevented. The detection limit of the mercaptans is currently about 50 ppbw, i.e. a proportion by weight of $50*10^{-9}$.

In the context of the present invention, the amount of hydrogen used in the process that must be observed is max. one (equimolar) with respect to the polyunsaturated hydrocarbons present in the hydrocarbon mixture. The molar ratio of hydrogen to the polyunsaturated hydrocarbons is preferably between 0.01 and 0.8. It is more preferably between 0.1 and 0.5.

A major advantage of this process is that the low hydrogen content means that 1-butene present in the C4 stream undergoes very little isomerization and remains available as a product of value. Only through the limits that must be strictly met for the amount of hydrogen present in the infeed is it possible to have a process in which mercaptans are etherified with polyunsaturated C4 hydrocarbons to high-boiling thioethers to concentrations below 50 ppbw without this being accompanied by hydrogenation of the monounsaturated butenes likewise present in the feed and by significant isomerization of the 1-butene. However, it is not possible for the hydrogen to be omitted altogether, since without hydrogen there is no conversion of mercaptans.

Another advantage of the process according to the invention is that it leads to complete conversion of mercaptans even in the presence of higher dienes.

The polyunsaturated hydrocarbons that are thioetherified with the mercaptans are preferably 1,3-butadiene and/or but-3-en-1-yne and/or 1,2-butadiene. These dienes and acetylenes are present particularly in FCC C4 only in small amounts and must in any case be fully hydrogenated downstream and are consequently no longer available as a product of value. In crack C4 streams with high 1,3-butadiene contents, the 1,3-butadiene is removed first in a separate process and utilized. The residual butadienes remaining in the C4 stream can then be used for the thioetherification.

A further particular advantage of the process is that, in addition to the highly reactive mercaptan methanethiol, higher mercaptans (for example ethanethiol) can also undergo reaction and thereby be removed.

Carbon monoxide may optionally be additionally added to the hydrocarbon mixture in the process. The content of carbon monoxide in the feed is in this case between 0.05 and 20 ppm carbon monoxide based on the mass of the hydrocarbon mixture. The amount of carbon monoxide added is preferably between 0.5 and 5 ppm. Metered amounts above 20 ppm do not improve the results further. The carbon monoxide is metered separately into the reactor or mixed in with the C4 stream that is fed in. Carbon monoxide can act as an additional moderator, reducing isomerization of 1-butene to 2-butenes.

The inlet temperature of the reactor feed is preferably in the range from 0 to 180° C., more preferably in the range from 60 to 150° C., particularly preferably in the range from 80 to 130° C. The pressure is preferably in the range from 2 to 50 bar, more preferably in the range from 6 to 40 bar, particularly preferably in the range from 10 to 30 bar. In a preferred embodiment, the hydrogen has been completely dissolved in the hydrocarbon stream. In this case, the pressure must be chosen so that the hydrogen remains completely dissolved and no gas phase develops in the reactor.

The thioetherification is preferably operated as a liquid-phase process. This means that all components are present at the catalyst in the liquid phase or are introduced into the reactor in liquid form. In particular, this means that the hydrogen and optionally also the carbon monoxide are completely dissolved in the liquid phase. Hydrogen is thus added to the hydrocarbon mixture to be hydrogenated in finely dispersed form and in amounts such that the liquid phase is always homogeneous before being fed into the reactor.

The hydrocarbon mixtures to be etherified may contain mercaptans and disulfides (if present) in the range from 0.01 to 200 ppm by weight. The thioetherification may be carried out in one or more reaction stages. If the content in the feed of mercaptans and disulfides (if present) is so high that the amount of hydrogen that is needed is no longer soluble in the feed, the feed may be diluted by circulation. Alternatively, the hydrogen may be added in several portions distributed over the length of the reactor or over the individual reaction stages.

After conversion of the mercaptans, including the mercaptans formed from the optionally present disulfides, into high-boiling thioethers, removal of these thioethers by distillation is possible. Through this, the thioether content of the remaining C4 hydrocarbon mixture can be reduced to below 50 ppb by weight. Together with a possible removal of low boilers upstream of the thioetherification reactor and distillation of high boilers downstream of the thioetherification reactor, this means that complete removal of all sulfur-containing components from the $C_4$ hydrocarbon mixture is possible.

The concentration of polyunsaturated olefins may be measured online by gas chromatography, allowing the amount of hydrogen to be set exactly from this. The same applies to the sulfur compounds.

The process is preferably used with mercaptan-containing mixtures of $C_4$ hydrocarbons originating from catalytic crackers (FCC C4) or steam crackers (crack C4). The C4 cut can of course be processed too.

The $C_4$ hydrocarbon mixture used as feed preferably initially undergoes removal of low-boilers, in particular of isobutane, by distillation. Alternatively, the process is employed prior to the removal of isobutane.

The present invention is elucidated hereinafter by way of examples. These examples are, however, selected purely as illustrative and should not be regarded as restrictive.

Example 1 (Non-Inventive)

A tubular reactor is filled with 540 ml of a catalyst containing 0.5% by weight of Pd on $Al_2O_3$. A C4 mixture is passed through the reactor at a continuous 4 kg/h at 90° C. and 20 bar pressure. The C4 mixture has the following composition:

0.5% by weight of 1,3-butadiene, 13.8% by weight of butane, 40.3% by weight of 2-butene, 20.3% by weight of 1-butene, 22.0% by weight of isobutene and 3.1% by weight of C5 hydrocarbons, and also 120 ppm by weight of isoprene, 2.8 ppm by weight of sulfur from ethanethiol and 6.0 ppm by weight of sulfur from dimethyl disulfide.

Metered into this mixture upstream of the reactor is 4.4 Nl/h of hydrogen. The composition of the discharge from the reactor is as follows:

0.4% by weight of 1,3-butadiene, 14.1% by weight of butane, 40.3% by weight of 2-butene, 20.3% by weight of 1-butene, 21.8% by weight of isobutene and 3.1% by weight of C5 hydrocarbons, and also 100 ppm by weight of isoprene, 0.7 ppm by weight of sulfur from ethanethiol and 2.2 ppm by weight of sulfur from dimethyl disulfide. Also detected were 1.5 ppm by weight of sulfur from methanethiol and 4.4 ppm by weight of sulfur from high-boiling compounds.

This corresponds to conversion of 75% of the ethanethiol, and also conversion of 38.3% of the dimethyl disulfide into high-boiling sulfur compounds and conversion of 25% of the dimethyl disulfide into methanethiol.

Full conversion of ethanethiol was not achieved, moreover with methanethiol a further mercaptan was formed from dimethyl disulfide.

Example 2 (Inventive)

A tubular reactor is filled with 540 ml of a catalyst containing 0.5% by weight of Pd and 0.2% by weight of Pt on $Al_2O_3$. A C4 mixture is passed through the reactor at a continuous 4 kg/h at 90° C. and 20 bar pressure. The C4 mixture has the following composition:

0.6% by weight of 1,3-butadiene, 12.3% by weight of butane, 40.5% by weight of 2-butene, 19.5% by weight of 1-butene, 23.8% by weight of isobutene and 3.3% by weight of C5 hydrocarbons, and also 95 ppm by weight of isoprene, 3.4 ppm by weight of sulfur from ethanethiol and 3.2 ppm by weight of sulfur from dimethyl disulfide.

Metered into this mixture upstream of the reactor is 4.4 Nl/h of hydrogen. The composition of the discharge from the reactor is as follows:

0.5% by weight of 1,3-butadiene, 12.6% by weight of butane, 39.5% by weight of 2-butene, 19.5% by weight of 1-butene, 24.6% by weight of isobutene and 3.3% by weight of C5 hydrocarbons, and also 80 ppm by weight of isoprene, 0.0 ppm by weight of sulfur from ethanethiol and 1.2 ppm by weight of sulfur from dimethyl disulfide, and also 5.4 ppm by weight of sulfur from high-boiling compounds.

No methanethiol was detected. This corresponds to conversion of 100% of the ethanethiol, and also conversion of 62.5% of the dimethyl disulfide into high-boiling sulfur compounds.

Through use of a catalyst according to the invention, the conversion of mercaptans was increased markedly compared with the non-inventive catalyst.

Example 3 (Non-Inventive)

A tubular reactor is filled with 540 ml of a catalyst containing 0.5% by weight of Pd and 0.2% by weight of Pt on $Al_2O_3$. The catalyst has the following characteristics, which were determined by CO pulse chemisorption according to AN-SOP 1954, version 1.

| | |
|---|---|
| Metal surface area [m$^2$/g] | 1.3 |
| Total amount of gas adsorbed [mmol/g] | 20.3 |
| Total metal dispersion [%] | 65 |

A C4 mixture is passed through the reactor at a continuous 4 kg/h at 90° C. and 20 bar pressure. The C4 mixture has the following composition:

0.7% by weight of 1,3-butadiene, 13.6% by weight of butane, 40.4% by weight of 2-butene, 20.3% by weight of 1-butene, 22.2% by weight of isobutene and 2.9% by weight of C5 hydrocarbons, and also 87 ppm by weight of isoprene, 5.1 ppm by weight of sulfur from ethanethiol and 5.1 ppm by weight of sulfur from dimethyl disulfide.

Metered into this mixture upstream of the reactor are 5.3 Nl/h of hydrogen. The composition of the discharge from the reactor is as follows:

0.4% by weight of 1,3-butadiene, 13.7% by weight of butane, 39.1% by weight of 2-butene, 20.8% by weight of 1-butene, 23.2% by weight of isobutene and 2.9% by weight of C5 hydrocarbons, and also 72 ppm by weight of isoprene, 1.4 ppm by weight of sulfur from ethanethiol and 1.7 ppm by weight of sulfur from dimethyl disulfide. Additionally detected were 0.9 ppm by weight of sulfur from methanethiol and also 6.2 ppm by weight of sulfur from high-boiling compounds.

This corresponds to a conversion of 72.5% of the ethanethiol, and also conversion of 35.3% of the dimethyl disulfide into high-boiling sulfur compounds and conversion of 17.6% of the dimethyl disulfide into methanethiol. Complete conversion of ethanethiol was not achieved, moreover the methanethiol means that an additional mercaptan was formed from dimethyl disulfide Example 4 (Inventive)

A tubular reactor is filled with 540 ml of a catalyst containing 0.5% by weight of Pd and 0.2% by weight of Pt on $Al_2O_3$. The catalyst has the following characteristics, which were determined by CO pulse chemisorption according to AN-SOP 1954, version 1.

| Metal surface area [m²/g] | 1.6 |
| Total amount of gas adsorbed [mmol/g] | 25.5 |
| Total metal dispersion [%] | 81.9 |

A C4 mixture is passed through the reactor at a continuous 4 kg/h at 90° C. and 20 bar pressure. The C4 mixture has the following composition:

0.7% by weight of 1,3-butadiene, 13.0% by weight of butane, 39.8% by weight of 2-butene, 19.2% by weight of 1-butene, 23.9% by weight of isobutene and 3.4% by weight of C5 hydrocarbons, and also 112 ppm by weight of isoprene, 5.7 ppm by weight of sulfur from ethanethiol and 5.4 ppm by weight of sulfur from dimethyl disulfide.

Metered into this mixture upstream of the reactor are 5.6 Nl/h of hydrogen. The composition of the discharge from the reactor is as follows:

0.4% by weight of 1,3-butadiene, 13.0% by weight of butane, 40.4% by weight of 2-butene, 18.9% by weight of 1-butene, 23.8% by weight of isobutene and 3.4% by weight of C5 hydrocarbons, and also 96 ppm by weight of isoprene, 0.0 ppm by weight of sulfur from ethanethiol and 0.7 ppm by weight of sulfur from dimethyl disulfide.

No methanethiol was detected. This corresponds to a conversion of 100% of the ethanethiol, and also conversion of 87% of the dimethyl disulfide into high-boiling sulfur compounds.

Example 5 (Inventive)

A tubular reactor is filled with 540 ml of a catalyst containing 0.5% by weight of Pd and 0.2% by weight of Pt on $Al_2O_3$. The catalyst has the following characteristics, which were determined by CO pulse chemisorption according to AN-SOP 1954, version 1.

| Metal surface area [m²/g] | 1.5 |
| Total amount of gas adsorbed [mmol/g] | 23.8 |
| Total metal dispersion [%] | 76 |

A C4 mixture is passed through the reactor at a continuous 4 kg/h at 90° C. and 20 bar pressure. The C4 mixture has the following composition:

0.6% by weight of 1,3-butadiene, 12.4% by weight of butane, 39.8% by weight of 2-butene, 19.9% by weight of 1-butene, 23.9% by weight of isobutene and 3.8% by weight of C5 hydrocarbons, and also 124 ppm by weight of isoprene, 3.3 ppm by weight of sulfur from ethanethiol and 2.2 ppm by weight of sulfur from dimethyl disulfide.

Metered into this mixture upstream of the reactor are 4.4 Nl/h of hydrogen. The composition of the discharge from the reactor is as follows:

0.4% by weight of 1,3-butadiene, 12.6% by weight of butane, 39.8% by weight of 2-butene, 19.7% by weight of 1-butene, 23.4% by weight of isobutene and 3.8% by weight of C5 hydrocarbons, and also 104 ppm by weight of isoprene, 0.0 ppm by weight of sulfur from ethanethiol and 0.6 ppm by weight of sulfur from dimethyl disulfide.

No methanethiol was detected. This corresponds to a conversion of 100% of the ethanethiol, and also conversion of 72.7% of the dimethyl disulfide into high-boiling sulfur compounds.

In the comparison of Examples 3 to 5, it is shown that complete conversion of the mercaptans cannot be achieved when using catalysts having a total metal dispersion of less than 70%. Complete conversion is only achieved in Examples 4 and 5 when the total metal dispersion on the catalyst is above 70%.

The invention claimed is:

1. A heterogeneous catalyst for complete conversion of mercaptans from hydrocarbon streams comprising C2 to C8 olefins, wherein a heterogeneous catalyst comprises a support material and catalytically active metal and the heterogeneous catalyst is a shell catalyst,
   and the support material is selected from the group consisting of alumina, silica gel and activated carbon and the catalytically active metals are palladium and platinum,
   and the heterogeneous catalyst has a palladium concentration of up to 2.0% by weight, a platinum concentration of up to 1.0% by weight and a total metal dispersion of at least 70%, and
   wherein the catalyst comprises an inner surface area of from 50 to 400 m²/g.

2. The heterogeneous catalyst according to claim 1, wherein the palladium concentration of up to 1.0% by weight and the hydrocarbon streams comprising C3 to C6 olefins,
   wherein the catalyst comprises an inner surface area of from 100 to 300 m²/g, and
   wherein the heterogeneous catalyst has a total metal dispersion of at least 80%.

3. The heterogeneous catalyst according to claim 1, wherein the platinum concentration of up to 0.5% by weight and the hydrocarbon streams comprise C4 olefins, and
   wherein the catalyst comprises an inner surface area of from 200 to 300 m²/g.

4. The heterogeneous catalyst according to claim 1, wherein the heterogeneous catalyst has a total metal surface area of at least 0.5 m²/g.

5. The heterogeneous catalyst according to claim 1, wherein the heterogeneous catalyst has a total metal dispersion of at least 80%.

6. The heterogeneous catalyst according to claim 1, wherein the palladium concentration of up to 0.5% by weight.

7. The heterogeneous catalyst according to claim 1, wherein the platinum concentration of up to 0.2% by weight.

8. The heterogeneous catalyst according to claim 1, wherein the heterogeneous catalyst has a total metal surface area of at least 1.0 m²/g.

9. A process for complete conversion of mercaptans from hydrocarbon streams in the presence of at least one higher diene by thioetherification of the mercaptans with polyunsaturated hydrocarbons, wherein the process is carried out in a reactor with addition of hydrogen, wherein the molar ratio of hydrogen to polyunsaturated hydrocarbons is not more than one, wherein a heterogeneous catalyst comprises a support material and a catalytically active metal used in the process comprises palladium and platinum as catalytically active metals, wherein the heterogeneous catalyst has a palladium concentration of up to 2.0% by weight, a platinum concentration of up to 1.0% by weight and a total metal dispersion of at least 70%.

10. The process according to claim 9, wherein the higher diene is a $C_5$ diene.

11. The process according to claim 9, wherein the mercaptans are thioetherified with polyunsaturated hydrocarbons, wherein the polyunsaturated hydrocarbons are selected from the group consisting of 1,3-butadiene, but-3-en-1-yne and 1,2-butadiene.

12. The process according to claim 9, wherein at least ethanethiol and/or methanethiol are present as mercaptans.

13. The process according to claim 9, wherein the molar ratio of hydrogen to polyunsaturated hydrocarbons is between 0.01 and 0.8.

14. The process according to claim 9, wherein it is carried out in the presence of carbon monoxide, wherein the content of carbon monoxide in the reactor feed is less than 20 ppm based on the mass of the feed.

15. The process according to claim 9, wherein the inlet temperature of the reactor feed is between 0° C. and 180° C.

16. The process according to claim 9, wherein it is operated as a liquid-phase process and that the hydrogen is dissolved completely in the liquid phase.

17. The process according to claim 9, wherein a $C_4$ hydrocarbon stream is used as feed for the reactor.

18. The process according to claim 9, wherein, if 1-butene is present in the hydrocarbon stream in a concentration that is higher than the concentration at thermodynamic equilibrium for the double bond isomerization of 1-butene to 2-butene, the conversion of 1-butene into 2-butenes through isomerization and/or the hydrogenation to n-butane is less than 5%.

19. The process according to claim 9, wherein the diene is a isoprene.

20. The process according to claim 9, wherein the molar ratio of hydrogen to polyunsaturated hydrocarbons is between 0.1 and 0.5.

* * * * *